United States Patent
Klaassen

(10) Patent No.: US 7,371,212 B2
(45) Date of Patent: May 13, 2008

(54) VAGINAL SPECULUM

(75) Inventor: Bernard Wilhelm Geziena Nicolaas Klaassen, Huissen (NL)

(73) Assignee: Comfortpat B.V. (NL)

( * ) Notice: Subject to any disclaimer, the term of this patent is extended or adjusted under 35 U.S.C. 154(b) by 0 days.

(21) Appl. No.: 10/533,624

(22) PCT Filed: Oct. 29, 2003

(86) PCT No.: PCT/NL03/00738

§ 371 (c)(1),
(2), (4) Date: Dec. 23, 2005

(87) PCT Pub. No.: WO2004/039252

PCT Pub. Date: May 13, 2004

(65) Prior Publication Data

US 2006/0122463 A1 Jun. 8, 2006

(30) Foreign Application Priority Data

Oct. 29, 2002 (NL) .................................. 1021773

(51) Int. Cl.
*A61B 1/32* (2006.01)
(52) U.S. Cl. ...................... 600/222; 600/220
(58) Field of Classification Search ................ 600/219, 600/220, 221, 222, 223, 224, 213
See application file for complete search history.

(56) References Cited

U.S. PATENT DOCUMENTS

| 872,344 | A | * | 12/1907 | Griswold | .................... 600/223 |
| 1,568,732 | A | * | 1/1926 | Haslinger | ................... 600/196 |
| 3,762,400 | A | | 10/1973 | McDonald | |
| 3,769,980 | A | | 11/1973 | Karman | |
| 4,502,468 | A | | 3/1985 | Burgin | |
| 4,638,792 | A | * | 1/1987 | Burgin | ....................... 600/212 |
| 4,971,036 | A | | 11/1990 | Collins | |
| 5,072,720 | A | | 12/1991 | Francis et al. | |
| 5,716,329 | A | | 2/1998 | Dieter | |
| 2001/0018550 | A1 | | 8/2001 | Boebel et al. | |

(Continued)

FOREIGN PATENT DOCUMENTS

CN 88 2 03700 10/1988

(Continued)

*Primary Examiner*—Cary E. O'Connor
(74) *Attorney, Agent, or Firm*—Greenberg Traurig, LLP

(57) ABSTRACT

The invention relates to a vaginal speculum comprising two spoon blades, which are intended for insertion into the vagina, and which are elongated and are located along side and opposite one another;—are mutually hinging in a clamped plane and through the longitudinal direction between a closed and open position; in which a handle is provided with operating means, in which the speculum is constructed in modular fashion with a first and a second module, the first module comprising the spoon blades, and the second module comprising the handle, and in which—the speculum further comprises transmission means that connect the operating means to the spoon blades, for opening and/or closing the spoon blades by means of the operating means; and in which—the speculum comprises connecting means, for connecting the first and second module together is a disconnectable manner. The invention also relates to an assembly comprising a second module for a vaginal speculum and two or more first modules for a vaginal speculum, the two or more first modules comprising at least two first modules with mutually differing dimensions.

11 Claims, 3 Drawing Sheets

U.S. PATENT DOCUMENTS

2002/0022771 A1   2/2002   Diokno et al.

FOREIGN PATENT DOCUMENTS

| CN | 2061038 | 8/1990 |
| WO | WO 98/25512 A | 6/1998 |
| WO | WO 01/47406 | 7/2001 |
| WO | WO 01/74418 A2 | 10/2001 |
| WO | WO 2004/039252 | 5/2004 |

* cited by examiner

000
VAGINAL SPECULUM

This application is a national stage filing under 35 U.S.C. 371 of International Application PCT/NL2003/000738, filed on Oct. 29, 2003, which claims priority from NL Application No: 1021773, filed on Oct. 29, 2002. The entire teachings of the referenced Applications are incorporated herein by reference. International Application PCT/NL2003/000738 was published under PCT Article 21(2) in English.

The present invention relates to a vaginal speculum comprising:

two spoon blades, which are intended for introduction into the vagina, which are elongated and are located alongside and opposite one another, and which are mutually hinging about a hinge with a hinge axis running in the widthwise direction of the spoon blades;

a handle module provided with operating means and a handle, the spoon blades being fixed detachably on the handle module.

Such a speculum is known from U.S. Pat. No. 3,769,980. This publication relates to a speculum in combination with a curette. The speculum is composed of a base part. The base part comprises two mutually hinging arms, which are each provided with a spoon blade on the distal end. Said spoon blades can each be disconnected individually from the respective arm. The spoon blades here form two parts that are separate from each other. The idea here is to replace the spoon blades after use.

WO 01/47406 discloses a speculum in which the handle is connected in a disconnectable manner to one of the two spoon blades. This means that when the speculum has been introduced into the vagina the handle is always connected to the spoon blades. A disadvantage of this is that the use of other examination means for internal examination, such as, for example, instrumentarium that is used for examination or treatment on or in the uterus and vagina, is restricted because of the space taken up by the handle.

It is true that detachable mirror or lighting means can be attached to the handle, but the possibilities or impossibilities for doing this are restricted through the specific embodiment of the handle.

The specula known from the prior art in general attempt to avoid the abovementioned disadvantage either by integrating lighting means or other examination means in the specific embodiment of the handle or by using the space that arises between the top and bottom part of the handle on opening of the speculum. In the design of a speculum the aim is therefore in general to keep this space as large as possible. It is also known from the prior art, namely from WO 98/25512, to place over the handle of a conventional speculum an attachment accessory, which accessory can have a light source.

Another disadvantage of the direct connection between the handle and one of the two spoon blades is that during the internal examination the handle is projecting all the time from the woman's body, which will generally be an unpleasant experience for her.

Yet a further disadvantage is that in the case of the conventional specula the entire speculum is generally either thrown away after use or is sterilized after use for reuse. Sterilization of the entire speculum has the disadvantage that the handle, which during use is generally much less heavily soiled than the part to be introduced into the vagina, is cleaned much more thoroughly than is strictly necessary. The disadvantage of throwing away the entire speculum is that a relatively large amount of material is wasted.

The object of the invention is to provide an improved speculum that preferably entirely, but at least partially, overcomes the abovementioned disadvantages, is more user-friendly and provides greater examination freedom for the doctor, or for the woman if it is a case of self-inspection.

This object is achieved according to the invention in the case of a speculum of the type indicated at the beginning by the fact that the speculum is constructed in modular fashion with the handle module and a spoon blade module;

by the fact that the spoon blades and the hinge are provided on the spoon blade module;

by the fact that the speculum further comprises:
   connecting means for connecting together in a disconnectable manner the handle module and the spoon blade module; and
   locking means for locking the spoon blades in an open position; and by the fact that the locking means are provided on the spoon blade module and comprise locking elements that are designed to hold the spoon blades locked in the open state in the vagina when the handle module of the spoon blade module is disconnected after the spoon blades have been introduced into the vagina and are in the open state.

The modular speculum according to the invention provides a number of considerable advantages. The greatest advantage is that after the disconnection of the handle module when the spoon blades have been introduced and are in the open state there is much more freedom to maneuver for examination or other operations. In view of the simple mechanical connection between handle module and spoon blade module—explained in greater detail in the description of the figures—it would also be possible to connect to the spoon blade module modules other than the handle module, such as, for example, a module with a special fiber optic or modules that facilitate the instrumentation, such as, for example, a part of an instrument, camera or endoscope as an aid.

Another advantage is that if the handle module is disconnected during the examination the possibility of contamination of it is prevented as far as possible.

Yet another advantage is that one handle module can be used in combination with various spoon blade modules. The relatively simple embodiment of the spoon blade module—see further in the description—means that it is even possible to choose to throw away the spoon blade module after use.

According to a further advantageous embodiment of the invention, the spoon blade module is provided externally with at least one surface that tapers relative to the longitudinal direction of the spoon blades in the distal direction of the latter, upon which surface, when the speculum has been introduced into the vagina, the sphincter vaginae can act in such a way that a force acting in the distal direction is exerted upon the speculum, which force holds the speculum in the vagina while the spoon blades are not yet spread.

The muscle tissue situated at the mouth of the vagina comprises in particular the musculus sphincter ani externus and the left-hand and right-hand parts of the musculus bulbocavernosus. The musculus bulbocavernosus together with the musculus sphincter ani externus forms a ring of muscle tissue surrounding the mouth of the vagina, further referred to as the sphincter vaginae. If the spoon blade module of the vaginal speculum according to the invention is of suitable size and shape, it is found that this ring of muscle tissue is capable of fixing this spoon blade module in the mouth of the vagina.

The specula used in practice have an assembly of spoon blades provided with external surfaces which, viewed in the longitudinal direction of the speculum, taper in the proximal direction and in this way form an application surface for a force for expelling the speculum, which force, as a result of the elastic properties of the muscle tissue in the vagina, is exerted upon a speculum that has been introduced.

The fact that the spoon blade module can be designed in many different ways for achieving the fixing effect aimed at according to the invention will be clear to a person skilled in the art, given the anatomy of the human body.

In order to simplify the manufacture of the spoon blade module, it is advantageous according to the invention, if the hinge comprises a strip of material with a flexibility that permits hinging. This makes it possible to have the spoon blade module made of one part—leaving aside the transmission means—for example by means of two-component injection molding, instead of separate spoon blades, which are connected, for example, by means of a hinge pin. This design has the advantage over a design with a hinge pin that there is less risk of the tissue becoming trapped between the spoon blades. Furthermore, such an embodiment reduces the production costs of the spoon blade module.

According to a further advantageous embodiment of the speculum according to the invention, the spoon blades are provided with protuberances on the outside at edge parts of the spoon blades that lie opposite each other when the spoon blades are closed. On closing of the spoon blades, said protuberances will push the wall of the vagina slightly further away at that point, so that the risk of the tissue becoming trapped between the spoon blades is considerably reduced.

In order to prevent possible contamination of the handle module by body fluids, the spoon blade module of the speculum is provided with a collection channel on the underside. It has already been said above that through disconnection of the handle during the examination, contamination of the spoon blade module is prevented as far as possible from spreading to the handle module. The collection channel will substantially prevent contamination from reaching the handle when the handle module is connected to the spoon blade module.

According to yet another advantageous embodiment of the invention, the handle module and the spoon blade module can be attached to each other by means of a connection consisting of slots in the end face of one of the two modules, on the one hand, and insertion parts on the end face of the other module, on the other hand, which insertion parts are inserted into the slots. Such a mechanical connection makes connection and disconnection of the handle module very easy and achievable with one hand. Furthermore, this means that it is relatively simple to design other modules, such as the abovementioned fiber optic module or modules that facilitate instrumentation, such as, for example, a part of an instrument, camera or endoscope, in such a way that they can be connected to the spoon blade module in a similar manner to that of the connection of the handle module.

Owing to the simple operation mechanism on the handle module for opening and closing of the spoon blades, the easy mechanical connection and disconnection of the handle module and the spoon blade module, and to the exertion of a force acting upon the speculum in the distal direction which holds the speculum in the vagina, the speculum according to the invention is pre-eminently suitable for self-inspection.

According to a further aspect, the invention relates to an assembly comprising the handle module and two or more spoon blade modules. In particular, it is an advantage here if the two or more spoon blade modules comprise at least two modules with mutually differing dimensions.

In combination with the abovementioned simple mechanical connection between spoon blade modules and handle module, in the event of a spoon blade module that is not an entirely good fit, during the internal examination it will be relatively easy to introduce another spoon blade module with a better fit.

This aspect of the invention, together with the abovementioned simple production method of the spoon blade module, also makes it possible to use disposable spoon blades.

The present invention will be illustrated in greater detail below with reference to appended drawings, in which.

Figure 1:
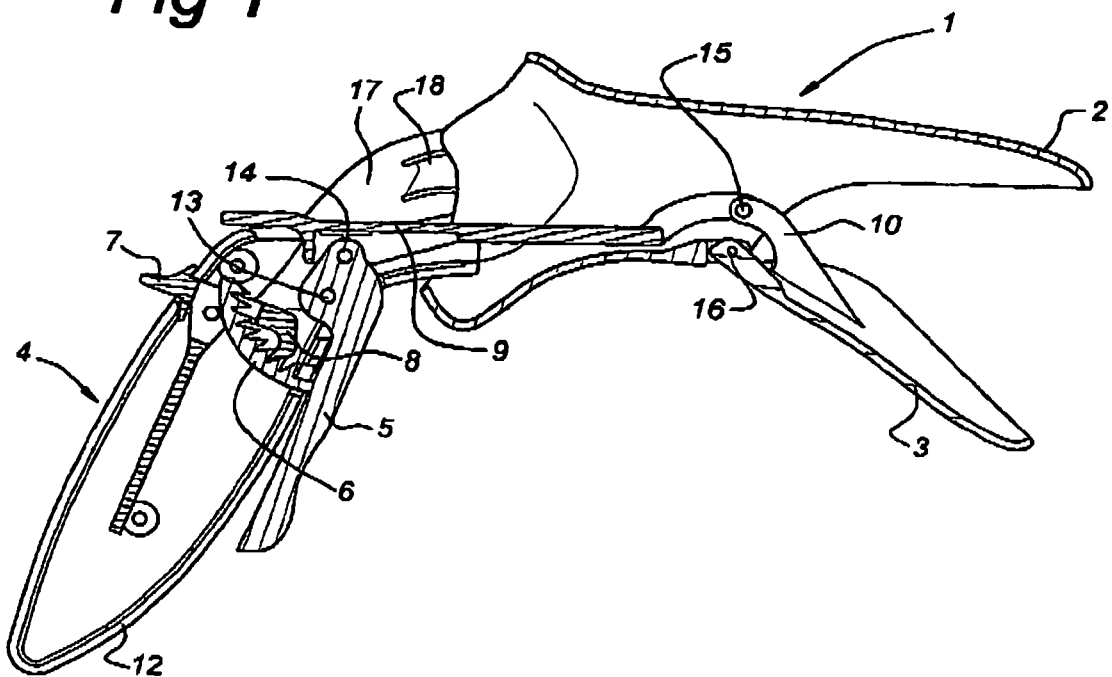
FIG. 1 shows diagrammatically the speculum in side view and partially in mid-longitudinal section, in the opened position of the spoon blades.
Figure 2:
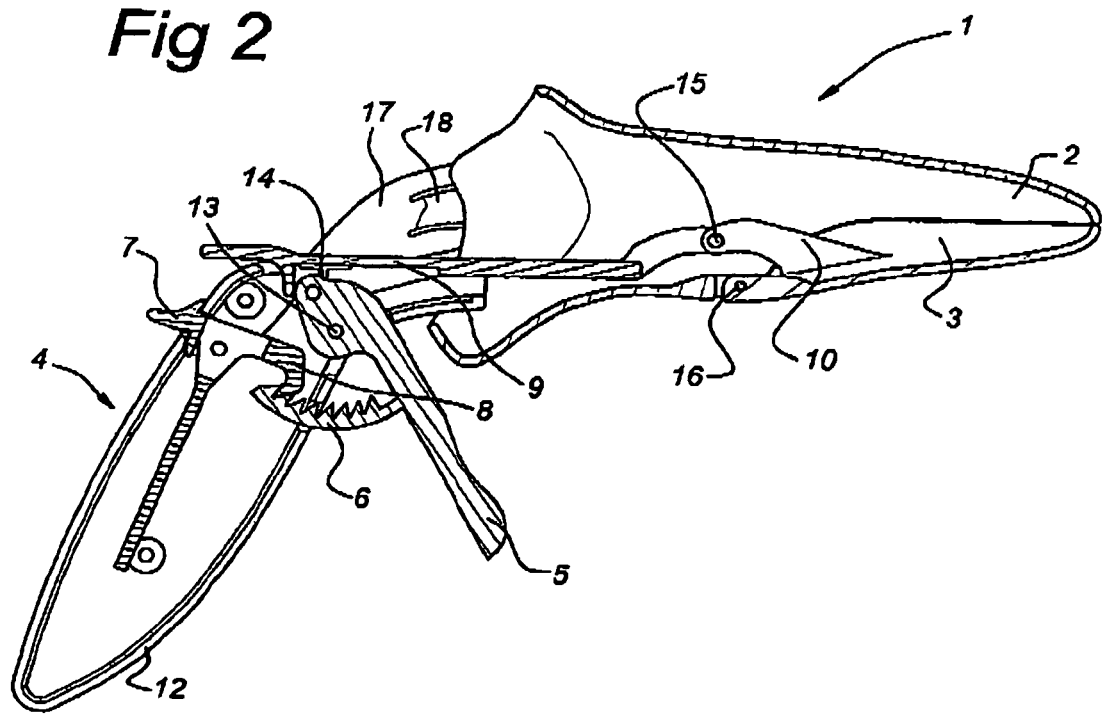
FIG. 2 shows diagrammatically the speculum in side view and partially in mid-longitudinal section, in the closed position of the spoon blades.

FIG. 1 shows the speculum according to the invention in side view, partially in cross section and with the spoon blades in an open position. FIG. 2 shows a similar view, but with the spoon blades in a closed position. In these figures the spoon blade module 1, with a top spoon blade 2 and a bottom spoon blade 3 and the handle module 4 are clearly distinguishable, The connection between the two modules will become clear from the description of FIGS. 3 and 4, but the opening and closing of the spoon blades will be explained first.

In FIGS. 1 and 2 the following can be distinguished in the handle module: an operating handle 5, a gear rack 6, a release button 7 and a tooth 8. These components together form the abovementioned operating means of the handle module. The following can be distinguished on the spoon blade module: a long transmission rod 9, and an arm 10 fixed on the bottom blade, which arm is hinged to the transmission rod 9. These parts together form the abovementioned transmission means.

When the operating handle 5 and the handgrip 12 of the handle module are squeezed toward each other—an operation which is pre-eminently suitable for operation with one hand—the operating handle will rotate about an axis 13. By means of a mechanical clutch 14, this rotation will be converted into a forward movement, in this case in the distal direction, or—better—translation of the transmission rod 9.

By way of a hinge 15, the arm 10 will move downwards and open the bottom spoon blade relative to the top spoon blade.

In the course of this operation the two spoon blades swing relative to hinge 16. In these figures the hinge is indicated as a hinge pin.

When the operating handle 5 and the handgrip 12 are squeezed together, the gear rack 6 will further move inwards toward the inside of the handgrip, with the result that the tooth 8 further engages with the is gear rack 6—in this case therefore in the direction of the operating handle 5—and fixes the fully or partially open position of the spoon blades. This mechanism becomes clear through comparison of the relative positions of the abovementioned parts in FIGS. 1 and 2 respectively.

The spoon blades are closed again by depressing the release button 7, with the result that the tooth 8 comes out of the teeth of the gear rack 6, the open position of the spoon blades is no longer fixed, and the spoon blades will close.

It depends on the specific embodiment of the speculum according to the invention whether this closure of the spoon blades occurs by itself or has to be brought about by means of an external force. Both embodiments are possible and in particular will depend on the exact design of the hinge between the two spoon blades. If the spoon blade module is of a suitable size and shape, when this module has been introduced into the vagina it will close by itself as a result of the elastic properties of the muscle tissue in the vagina. The choice is therefore whether an embodiment is selected that is such that on depression of the release button 7 the spoon blades close by themselves even in a position not introduced into the vagina. In the closed position of the spoon blades shown in FIG. 2 the spoon blades 2 and 3 are resting substantially against each other. A slight gap can be present between the spoon blades 2 and 3, in order to prevent tissue from becoming trapped between the two spoon blades when the latter go from an open to a closed position.

Other parts that can be distinguished in FIGS. 1 and 2 are a raised edge 17 (part of and directly connected to handgrip 12) and an insertion part 18, which forms part of the raised edge 17.

Figure 3:
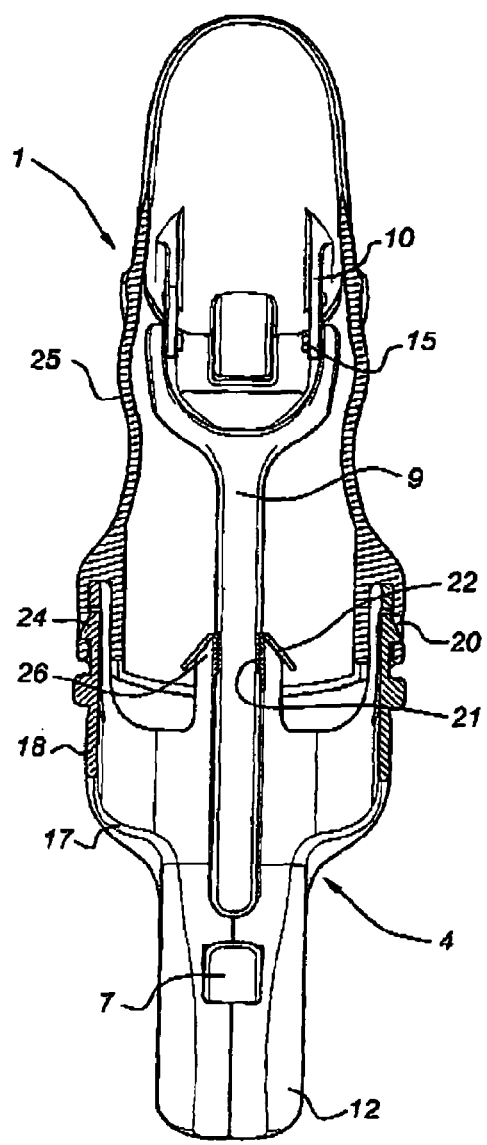
FIG. 3 shows a diagrammatic top view of the speculum, partially in cross section, with handle module and spoon blade module connected to each other.
Figure 4:
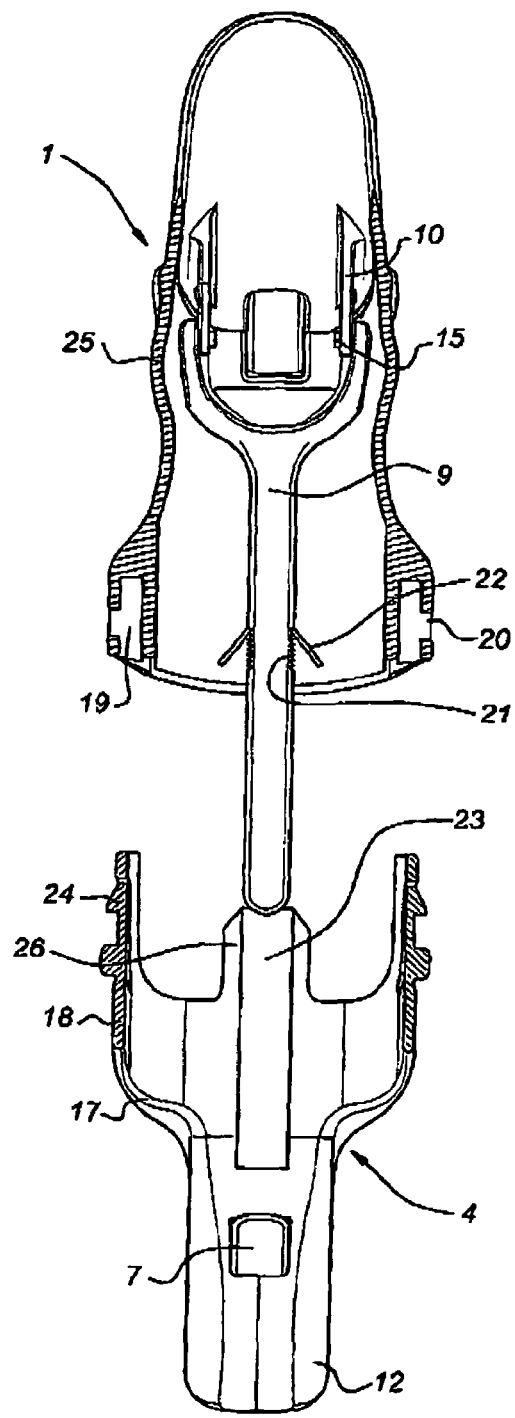
FIG. 4 shows a diagrammatic top view of the speculum, partially in cross section, with handle module and spoon blade module disconnected from each other.

FIGS. 3 and 4 show a diagrammatic top view of the speculum according to the invention in the connected position (FIG. 3) and disconnected position (FIG. 4) respectively of the spoon blade module and handle module. Apart from the known, defined parts, the following can be distinguished on the spoon blade module in these figures: two slots 19 on the end face, an opening in said slot in open communication with the side of the module 20, a part of the transmission rod 9 with a tooth system 21, and a fixing means 22. The last two parts—tooth system and fixing means—together form the abovementioned locking elements.

The following can further be distinguished on the handle module in FIGS. 3 and 4; an opening 23, a wedge-shaped projection 24 on the end of the insertion part 18, and a bend-away part 26. The insertion part 18 is connected to the handle in such a way that said insertion part can move up and down elastically in the vertical direction relative to the raised edge 17.

These parts provide the mechanical connection of the two modules. The two insertion parts 18 are slid into slots 19, and the insertion part 18 will move elastically inwards relative to the outside wall of the slot until the projection goes into the opening and becomes fixed there. Pushing the insertion parts 18 inwards causes the projection 24 to be released again from the opening 20, and the insertion parts can be pushed out of the slots again in order to disconnect the handle from the spoon blade module again. The transmission rod 9 is part of the spoon blade module and slides into the special opening 23 on the handle module. Other connections are also readily conceivable, such as, for example, a bayonet connection.

During the opening of the spoon blades the fixing means 22 acts upon the tooth system 21 of the transmission rod 9 and causes fixing of the open position of the spoon blades. Since the transmission rod 9 with the tooth system and the fixing means 22 is part of the spoon blade module, the open position of the spoon blades remains fixed during the disconnection and connection of the handle module. The bend-away means 26 ensures that on connection to the spoon blade module the fixing means 22 is bent away, with the result that the fixing function is taken over by the gear rack 6 and tooth 8 of the handle. The fixing means 22 according to the invention is further designed in such a way that in a disconnected state of the handle the fixing means can also be bent away from the tooth system 21 by hand. In particular, this operating mechanism is placed in a proximal position, in order to make it easy to reach, and it can be operated with one hand. This is something of a precautionary measure, in the sense that for this the spoon blades in a position introduced into the vagina are also easy to close when the handle is disconnected.

In the top view of FIGS. 3 and 4 a surface 25 that tapers in the distal direction relative to the longitudinal direction of the spoon blades is shown. This surface ensures that a force acting in the distal direction is exerted, which force holds the speculum in the vagina. According to the invention it is not necessary for this surface to be provided at exactly this position, or for it to have exactly this shape.

Figure 5:
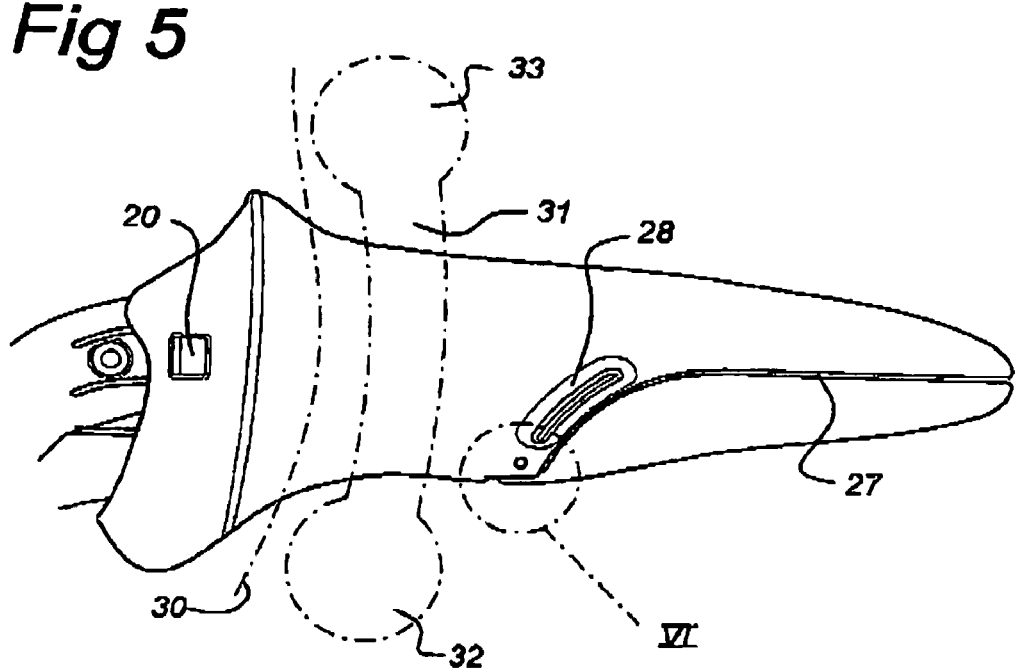
FIG. 5 shows the spoon blade module in side view, with the bottom and top spoon blades connected by means of a hinge pin.

FIG. 5 shows the spoon blade module in side view with the spoon blades in the closed position. The position of the opening 20 can be seen clearly in this figure. The shape of and the connection 27 between the two spoon blades can also be distinguished in this figure.

FIG. 5 further shows the position of the abovementioned protuberance 28 on the edge of the top spoon blade. For the function of these protuberances—in the main preventing vaginal tissue from being trapped during closure of the spoon blades—it is not necessary according to the invention for the protuberance to be provided on the top spoon blade. Such a protuberance can be produced relatively easily by, for example, adapting an injection mold to it.

Figure 6:
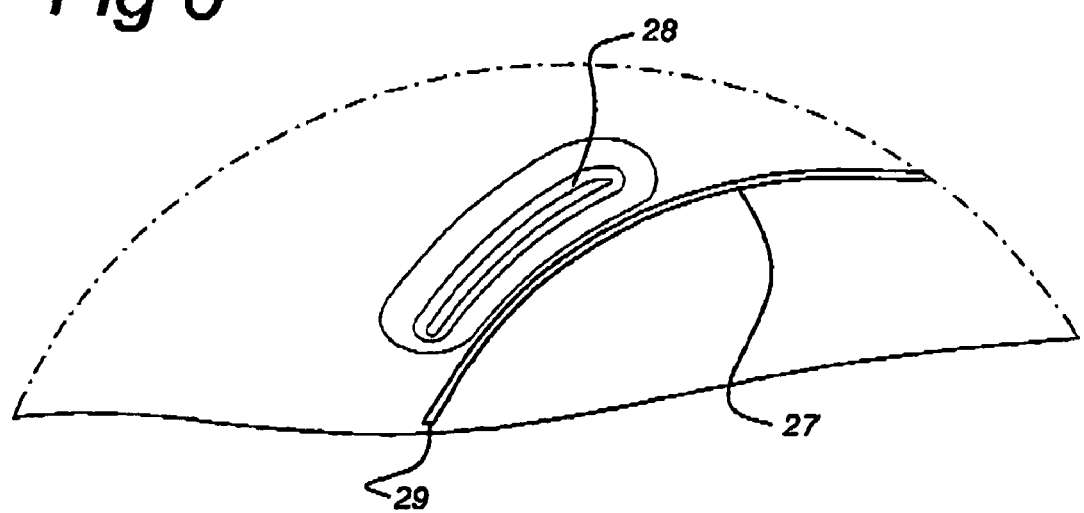
FIG. 6 shows an enlarged detail of section VI from FIG. 5, with the bottom and top spoon blades connected by means of a hinged strip of material.

FIG. 6, an enlarged detail of section VI from FIG. 5, shows a possible specific embodiment of the speculum according to the invention. In this case a strip of material 29 with a flexibility that permits hinging movement is used over a part of the cross section at the position of the hinges.

The advantage is that in that case the two spoon blades form a part that can be manufactured in one process step, for example by means of two-component injection molding.

The dotted line 30 in FIG. 5 shows diagrammatically the boundary between the inside and outside part of the spoon blade module. This makes it clear that the bottom spoon blade and the hinged part with the hinge are situated entirely in the inside part. According to the invention, this is preferable because during spreading of the spoon blades the mouth of the vagina, in particular the fleshy ring of muscle tissue, undergoes little or no stretching, which improves the user-friendliness.

As shown in FIG. 5, a ring of muscle tissue, the sphincter vaginae, is situated at the mouth of the vagina, consisting of the left-hand and right-hand part of the musculus bulbocavernosus 31 and the musculus sphincter ani externus 32. The musculus bulbocavernosus has on its top side an attachment to the pubic bone 33 and on its underside is connected to the musculus sphincter ani externus 32. The sphincter vaginae circumscribes the mouth of the vagina, and on tensing will fix the speculum according to the invention. This tensing can occur passively through stretching of the sphincter vaginae with the spoon blade module of the speculum and/or actively by tensing of the sphincter vaginae.

The invention claimed is:

1. A vaginal speculum comprising:
   two spoon blades, which are intended for introduction into the vagina, which are elongated and are located alongside and opposite one another, and which are mutually hinging about a hinge with a hinge axis running in the widthwise direction of the spoon blades;
   a handle module provided with operating handle and a handgrip, the spoon blades being fixed detachably on the handle module,
   wherein the speculum is constructed in modular fashion with the handle module and a spoon blade module;
   wherein spoon blades and the hinge are provided on the spoon blade module;
   wherein the speculum further comprises:
      a connecting means for connecting together in a disconnectable manner the handle module and the spoon blade module; and
      locking means for locking the spoon blades in an open position; and
      transmission means for transmitting movement of the operating handle into relative swinging of the spoon blades;
   wherein the transmission means are provided on the spoon blade module
   wherein the locking means are provided on the spoon blade module and comprise locking elements that are designed to hold the spoon blades locked in the open state in the vagina when the handle module is disconnected from the spoon blade module after the spoon blades have been introduced into the vagina and are in the open state.

2. The vaginal speculum as claimed in claim 1, in which the locking elements can be disconnected.

3. The vaginal speculum as claimed in claim 1, in which the spoon blade module is provided externally with at least one surface that tapers relative to the longitudinal direction of the spoon blades in the distal direction of the latter, upon which surface, when the speculum has been introduced into the vagina, the sphincter vagina can act in such a way that a force acting in the distal direction is exerted upon the speculum, which force holds the speculum in the vagina.

4. The vaginal speculum as claimed in claim 1, in which the hinge is situated in the vagina when the spoon blades have been introduced into the vagina, and in which the hinge is provided on the underside of the spoon blade module.

5. The vaginal speculum as claimed in claim 1, in which the hinge comprises a strip of material with a flexibility that permits hinging.

6. The vaginal speculum as claimed in claim 1, in which the spoon blades are provided with protuberances on the outside at edge parts of the spoon blades that rest against each other—or face each other—when the spoon blades are closed.

7. The vaginal speculum as claimed in claim 1, in which the spoon blade module is provided with a collection channel on the underside.

8. The vaginal speculum as claimed in claim 1, wherein the handle module and the spoon blade module are attached to each other by a connection consisting of slots in the end face of one of the two modules, on the one hand, and insertion parts on the end face of the other module, on the other hand, which insertion parts are inserted into the slots.

9. An assembly comprising a vaginal speculum as claimed in claim 1, further comprising two or more spoon blade modules.

10. The assembly as claimed in claim 9, in which the two or more spoon blade modules comprise at least two spoon blade modules with mutually differing dimensions.

11. The assembly as claimed in claim 1, in which the transmission means comprises a transmission rod extending through the spoon blade module and adapted for translation in its longitudinal direction, in which the locking means comprise a tooth system provided on the transmission rod and fixing means acting upon the tooth system for fixing, in a disconnectable manner, the transmission rod with respect to the spoon blade module.

* * * * *